United States Patent [19]

Daghighian et al.

[11] Patent Number: 5,325,855
[45] Date of Patent: Jul. 5, 1994

[54] FLEXIBLE INTRAOPERATIVE RADIATION IMAGING CAMERA

[75] Inventors: Farhad Daghighian, New York; Saul Miodownik, West Hempstead; Peter Shenderov, Brooklyn; Behzad Eshaghian, New York, all of N.Y.

[73] Assignee: Memorial Hospital For Cancer And Allied Diseases, New York, N.Y.

[21] Appl. No.: 927,156

[22] Filed: Aug. 7, 1992

[51] Int. Cl.[5] ............................................. A61B 5/05
[52] U.S. Cl. .................. 128/653.1; 128/654; 128/659; 250/368
[58] Field of Search .................. 128/653.1, 654, 659; 250/366, 367, 368; 378/38

[56] References Cited

U.S. PATENT DOCUMENTS

| | | |
|---|---|---|
| H801 | 7/1990 | Koechner et al. |
| 4,142,101 | 2/1979 | Yin |
| 4,145,610 | 3/1979 | Perilhou |
| 4,415,810 | 11/1983 | Brown, Sr. |
| 4,595,014 | 6/1986 | Barrett et al. ............ 128/659 |
| 4,753,512 | 6/1988 | Aurouet et al. |
| 4,755,681 | 7/1988 | Oka et al. |
| 4,788,436 | 11/1988 | Koechner |
| 4,791,300 | 12/1988 | Yin |
| 4,831,263 | 5/1989 | Yamashita ............ 250/368 |
| 4,837,439 | 6/1989 | Genna et al. |
| 4,845,769 | 7/1989 | Burstein et al. |
| 4,929,835 | 5/1990 | Yamashita et al. ......... 250/367 |
| 4,931,646 | 6/1990 | Koechner |
| 4,931,647 | 6/1990 | Hiruma et al. |
| 4,933,961 | 6/1990 | Rushbrooke et al. |
| 4,939,464 | 7/1990 | Hammer |
| 4,942,302 | 7/1990 | Koechner |
| 5,006,714 | 4/1991 | Attix |
| 5,008,546 | 4/1991 | Mazziotta et al. |
| 5,091,650 | 2/1992 | Uchida et al. ............ 250/368 |
| 5,118,934 | 6/1992 | Harley et al. ............ 250/368 |
| 5,118,940 | 6/1992 | Davis et al. ............ 250/368 |

OTHER PUBLICATIONS

Yasillo et al., *Design Considerations For A Single Tube Gamma Camera*, IEEE Transactions On Nuclear Science, vol. 2, pp. 609–615, Apr. 1990 (Exhibit 19).

Redus et al., *Interoperative Nuclear Imaging Probe*, IEEE Publication No. 0-7803-0513, pp. 1887–1891, Feb., 1991 (Exhibit 20).

Ljunggren and Strand, *Beta Camera For Static And Dynamic Imaging Of Charged–Particle Emitting Radionuclides in Biologic Samples*, The Journal of Nuclear Medicine, vol. 31, No. 12, pp. 2058–2063, Dec. 1990 (Exhibit 21).

Moore et al., *A Handheld, Low Power, Gamma Camera: Design Considerations And Initial Results*, Abstract from Proceedings Of The 35th Annual Meeting, The Journal of Nuclear Medicine, p. 832, date unknown (Exhibit 22).

*Characteristics And Applications Of Microchannel Plates*, Hamamatsu Technical Manual, RES-0795, Jan., 1987 (Exhibit 23).

(List continued on next page.)

Primary Examiner—Lee S. Cohen
Assistant Examiner—Brian L. Casler
Attorney, Agent, or Firm—John P. White

[57] ABSTRACT

An imaging apparatus with a flexible light guide which a surgeon can easily manipulate within the patient to control the field of view. Specifically, a scintillator receives radiation rays and converts these radiation rays into light signals at a position inside the body. A flexible bundle of optical fibers optically connected to the scintillator, channels the light signals from the scintillator to a position sensitive light signal detector located outside the body. The position sensitive light signal detector creates a digital signal to relay the position information about the detected event to a computer which accumulates these digital signals, converts these digital signals into images and displays the images.

9 Claims, 4 Drawing Sheets

OTHER PUBLICATIONS

*Microchannel Plates (MCPs)*, Hamamatsu Technical Data Sheet, Jul. 1985 (Exhibit 24).

*Circular MCP And Assembly Series*, Hamamatsu Technical Data No. T-114, Dec., 1987 (Exhibit 25).

*Crossed Wire Anodes Position-Sensitive Phtomultiplier Tubes R2486 Series*, Hamamatsu Technical Data Sheet, Oct., 1986 (Exhibit 26).

*PIAS—Photo-counting Image Acquisition System*, Hamamatsu brochure, May 1985 (Exhibit 27).

Barber et al., *Small Radiation Detectors For Bronchoscopic Tumor Localization*, IEEE Transactions on Nuclear Science, vol. NS-27, No. 1, pp. 496-502, Feb. 1980 (Exhibit 28).

Woolfenden, et al., *Lung Cancer Detection Using a Miniature Sodium Iodide Detector and Cobalt-57 Bleomycin*, Chest, vol. 85, pp. 84-88, Jan. 1984 (Exhibit 29).

Woolfenden and Barber, *Radiation Detector Probes For Tumor Localization Using Tumor-Seeking Radioactive Tracers*, American Journal of Roentgenology, vol. 153, pp. 35-39, Jul. 1989 (Exhibit 30).

Martin et al., *Intraoperative Radioimmunodetection of Colorectal Tumor With A Hand-Held Radiation Detector*, The American Journal Of Surgery, vol. 150, pp. 672-675, Dec. 1985 (Exhibit 31).

O'Dwyer et al., *Intraoperative Probe-Directed Immunodetection Using A Monoclonal Antibody*, Arch. Surg., vol. 121, pp. 1391-1394, Dec. 1986 (Exhibit 32).

Martin et al., *Radioimmunoguided Surgery Using Monoclonal Antibody,*, The American Journal Of Surgery, vol. 156, pp. 386-392, Nov. 1988 (Exhibit 33).

Sardi et al., *Intra-abdominal Recurrence Of Colorectal Cancer Detected By Radioimmunoguided Surgery (RIGS System)*, Arch. Surg., vol. 124, pp. 55-59, Jan. 1989 (Exhibit 34).

Nieroda et al., *The Impact Of Radioimmunoguided Surgery (RIGS TM) On Surgical Decision-Making In Colorectal Cancer*, Diseases Of The Colon and Rectum, vol. 32, No. 11, pp. 927-932, Nov. 1989 (Exhibit 35).

Reinhardt et al., *Topographic Studies With $^{32}P$ Tumor During Operations Of Brain Tumors*, Eur. Surg. Res., vol. 17, pp. 333-340, 1985 (Exhibit 36).

Reinhardt et al., *A Computer-Assisted Device For The Intraoperative CT-Correlated Localization Of Brain Tumors*, Eur. Surg. Res., vol. 20, pp. 51-58, 1988 (Exhibit 37).

Barber et al., *Comparison Of In Vivo Scintillation Probes And Gamma Camera For Detection Of Small, Deep Tumors*, Phys. Med. Biol., vol. 34, No. 6, pp. 727-739, 1989 (Exhibit 38).

Hinkernell et al., *Dual-Detector Probe For Surgical Tumor Staging*, Journal Of Nuclear Medicine, vol. 29, No. 6, pp. 1101-1106, Jun. 1988 (Exhibit 39).

Hartsough et al., *Probes Containing Gamma Radiation Detectors For In Vivo Tumor Detection And Imaging*, Presented at OE-LASE '89 in Los Angeles, Calif. (to be published in SPIE vol. 1068) (Exhibit 40).

Hinkle et al., *The Evolution Of The Radioimmunoguided Surgery TM System: An Innovative Technique For The Intraoperative Detection Of Tumor, Antibody, Immunoconjugates, And Radiopharmaceuticals*, vol. 4, No. 3, pp. 339-358, 1991, (Exhibit 41).

Hinkernell et al., *Probability Modelling Of A Surgical Probe For Tumor Detection*, Phys. Med. Biol., vol. 35, No. 4, pp. 539-559, 1990 (Exhibit 42).

Aitken et al., *A Gamma-Detecting Probe For Radioimmune Detection Of CEA-Producing Tumors,*, Diseases Of The Colon & Rectum, vol. 27, No. 5, pp. 279-282, May 1984 (Exhibit 43).

FLEXIBLE INTRAOPERATIVE RADIATION IMAGING CAMERA

BACKGROUND OF THE INVENTION

This invention relates to an imaging apparatus for use during surgery to locate radiation marked tissue and to create an image of the marked tissue.

Within this application several publications are referenced by arabic numbers enclosed within parentheses. Full citations for these and other references may be found at the end of the specification immediately preceding the claims. The disclosures of all of these publications in their entireties are hereby incorporated by reference into this application in order to more fully describe the state of the art to which this invention pertains.

Precise surgical removal, frequently combined with radiation and chemotherapy, is the most widely used approach in the treatment of adults with solid cancers. Residual subclinical tumor deposits, which may be as large as 1 cubic centimeter even after laparotomy, chemotherapy and radiation can lead to failure in the treatment of patients with primary tumors and inadequate or inappropriate surgery in patients undergoing surgery for recurrent cancer. For example, each year in the United States 155,000 new colorectal cases undergo surgery. Current scanning with computerized tomography and magnetic resonance imaging combined with operative evaluation remain inadequate to determine the true extent of the disease. Although it appears likely that external imaging of radiolabeled antibodies could detect tumor deposits weighing 2-3 grams, a truly useful system must be able to detect tumors weighing less than 1 gram. Therefore, there is a need to develop tools for identifying subclinical tumor deposits at the time of laparotomy.

This need is particularly great for ovarian cancer. Detection of subclinical residual ovarian cancer following chemotherapy is one of the most pressing problems in the management of the 16,000 cases that occur each year in the United States. Recent studies indicate that 50% of patients determined to be free of tumor by standard surgical exploration actually harbor occult residual disease. New monoclonal antibodies have been developed which are highly specific for ovarian cancer. This disease lends itself well to the radioactive marker approach because the cancer tends to remain confined to the surface of the peritoneal cavity and retroperitoneal lymph nodes and because frequent laparotomies, over 300 of which are performed each year at the Memorial Sloan-Kettering Cancer Center, for example, are required as part of its clinical management. Therefore, the ability to detect subclinical residual disease with the use of intraoperative radiation detecting equipment would present a major advance in the management of this disease.

Recent advances have been made in the field of radioimmunolocalization of tumors using radioactive labeled monoclonal antibodies. For example, in one study monoclonal antibody MX35, which reacts with epithelial ovarian cancer, was labeled with Iodine-131. The labeling efficiency of the radioantibody was 92.6%. Three nude mice of the type balb c/nu/nu were injected intraperitoneally and subcutaneously at six weeks of age with serous human ovarian cancer cell line PR-428. This cell line immunohistologically expresses the MX35 antigen. The experiment was performed when the resulting tumors weighed approximately 0.5-2.0 grams. In the experiment, 25 microcuries of Iodine-131 per 25 milligrams of labeled antibody were injected intravenously into the tail vein. A beta probe then measured the radiation emitted at 2, 5 and 7 days after the injection of the marker. The tip of the probe was placed on the surface of the skin at different locations on the body for 20 seconds. The probe counted an average of 6.5 counts/second on the tumor versus an average of 0.5 counts/second on normal tissue. The corresponding tumor sites were verified by surgery. The concentration of the monoclonal antibody were 10 times higher in the tumor than the normal tissue. Thus, this experiment demonstrates the feasibility of detecting a tumor through beta radiation even when there is intervening tissue covering the tumor. Nevertheless, the probe would have to be moved repeatedly to comprehend the extent of each tumor.

As exemplified by this study, a probe for beta rays is known in the prior art, see, for example, U.S. Pat. No. 5,008,546 ("'546") to Mazziotta et al. Since the beta probe of Mazziotta et al. '546 is sensitive only to beta rays, a beta probe in close proximity to the tissue can image small superficial tumor deposits without any interference from background gamma rays. Background gamma radiation can obscure the radiation normally received from beta markers. However, scanning a large area, for example, the surface of the peritoneal cavity, with a beta probe during surgery may be too time consuming. Therefore, a wider field of detection is needed.

Other studies discuss difficulties with background radiation. Barber et al. and Woolfenden et al. (1-3) developed and used several intraoperative and intraluminal gamma probes for gynecologic and lung tumor detection using Cobalt-57 labeled bleomycin as a tumor marker. These attempts were only partially successful due mainly to the background gamma rays emitted from distant organs with high radioactive uptake. A Cadmium-Tellurium semiconductor gamma detector, for example, can be used. Such a detector is commercially available from the Neoprobe Corporation of Columbus, Ohio. This detector is 15 millimeters in diameter and 2 millimeters thick. Due to its thinness, the detector is only efficient in detecting relatively low energy gamma rays or X-rays, for example, X-rays of 30 kiloelectron volts emitted from Iodine-125. This severely limits the application of this probe to only isotopes that emit low energy gamma rays or X-rays. Since these low energy gamma rays are less effective in penetrating tissue than higher energy gamma rays, the problem of background activity is reduced somewhat. Accordingly, several groups that have used such a device in surgery were successful in locating tumors (4-8). Dr. A. Cohen of the Memorial Sloan-Kettering Cancer Center recently reported the experience of a multicenter trial with the Neoprobe detector in 105 patients using Iodine-125 labeled with B72.3 monoclonal antibodies confirming the previous work. However, this detector is still sensitive to background radiation. Additionally, the Neoprobe detector is very sensitive to temperature changes and to background radiation when pointed at a highly radioactive area. Also, this probe is too large for sites within a small operative field.

As exemplified in these studies, intraoperative gamma cameras and probes are known in the art, see for example, U.S. Pat. No. 4,791,300 ("'300") to Yin. However, Yin '300 is designed to detect only gamma radiation which travels much farther in tissue than some other types of radiation, such as beta rays. Therefore, there is a need for a camera that can be placed very close, that is, within millimeters of the source of the radiation. Additionally, if a camera could be placed close to the source of radiation, the effects of background radiation are reduced.

In another study, Reinhardt et al. (9, 10) used a semiconductor detector to localize tumor remnants which were visually difficult to distinguish from normal brain tissue. Reinhardt et al. used P-32 as a tumor marker. This isotope emitted only beta rays and not gamma rays. Most other beta emitting isotopes emit gamma emissions as well; therefore a semiconductor probe would still have the difficulty of any other gamma probe when used with commonly used isotopes for tumor marking that emit gamma rays in addition to beta rays, for example, Iodine-131. Additionally, they were not successful in detecting highly malignant brain cancers because P-32 was not a good tumor marker. They concluded that other specific tumor markers such as monoclonal antibodies are needed.

In another recent study, Barber et al. (11) compared a Sodium-Iodine-Thallium gamma probe with a gamma camera for the task of detecting radiolabeled tumors in a water phantom. They concluded that 15 seconds of counting with a gamma probe located a few centimeters away is superior to 10 minutes of imaging with a conventional gamma camera placed 10–20 centimeters from the source when the background radiation is uniform. This study also showed that if the conventional gamma camera is positioned less than 5 centimeters from the source, tumor detectability would improve substantially. Also, Hickernell et al. (12) developed a dual, coaxial, Sodium-Iodine-Thallium gamma probe in order to take account of the background counts by using an outer detector. Based on computer simulations this probe should be more effective in identifying tumors only if the probe is centered on the tumor. Additionally, Hartsough et al. (13) have built an imaging probe using a two dimensional array of 21 Cadmium-Tellurium detectors, where each detector has dimensions of 3 millimeters by 3 millimeters and the detectors are located behind a parallel hole collimator. Although this imaging probe has low efficiency due to its collimator and has only 21 imaging elements which are not sufficient to form a realistic image, this imaging probe is expected to improve the discrimination of tumor counts from background counts. These studies also show the efficacy of placing the camera's detector element as close as possible to the area of interest. Although these cameras and probes present partial solutions to reduce the effects of background radiation, each of these devices have their own limitations.

Finally, beta cameras which are less sensitive to gamma radiation are known in the art. For example, see Ljundggren and Strand (14). The Ljundggren and Strand camera, which is constructed with a scintillator, a rigid fiber optic face plate, a photocathode, a microchannel plate and a resistive anode, however, is too large and inflexible to be used in conjunction with a laparoscopic procedure. Also, the microchannel plate of the Ljundggren and Strand camera uses 10,000 volts of electricity making the camera relatively dangerous for intraoperative use. Additionally, this tabletop camera was built for in-vitro imaging of laboratory animal tissues.

SUMMARY OF THE INVENTION

The present invention overcomes these and other limitations by providing a hand held beta camera with a long and flexible bundle of optical fibers for intraoperative use inside the patient to facilitate tumor identification and removal.

By being small, flexible, and capable of imaging, this instrument will be ideal for detection of tumors in surgical procedures involving small incisions, for example, laparotomy with a laparoscope and for hard-to-reach areas.

This invention provides an imaging apparatus for creating images of radiation emitting objects during surgical operations, comprising a scintillator for receiving radiation rays and converting the radiation rays into light signals at a first position, a flexible bundle of optical fibers optically connected at the first position to the scintillator for channelling the light signals from the first position to a second position spaced from the first position and a position sensitive light signal detector optically connected to the flexible bundle of optical fibers at the second position for receiving the light signals and for producing images of the radiation emitting object, whereby the scintillator may be flexibly moved relative to the position sensitive light detector during surgical operations.

This invention also provides a position sensitive light signal detector which can comprise a photocathode for receiving the light signals and converting the light signals into electronic signals, an electronic signal amplifier for amplifying the electronic signals, a position sensitive anode for receiving the amplified electronic signals, determining the location where each light signal was received on the photocathode and for producing location signals and a circuit for receiving the location signals and for producing an image of the radiation emitting object.

Also, the invention provides a position sensitive light signal detector which can comprise a position sensitive photomultiplier tube for producing location signals indicative of where each light signal was received and a circuit for receiving the location signals and for producing an image of the radiation emitting object.

This invention also provides a scintillator which can comprise a thin film plastic scintillator sensitive to beta radiation and resistant to gamma radiation.

Also, this invention provides a flexible bundle of optical fibers which can have a cross-section smaller than the cross-section of the position sensitive light detector, and wherein the flexible bundle of optical fibers is optically connected proximate to the center of a receiving surface of the position sensitive light detector.

This invention also provides a circuit which can comprise an electronic circuit for receiving the location signals, for converting the location signals into digital signals which correspond to the positions where beta rays impact the plastic scintillator film and for transmitting the digital signals and a computer for receiving, accumulating, manipulating and displaying the digital signals such that the computer enables image production, image storage, image comparisons, image combinations and image display.

Also, this invention provides a surgical apparatus for removing or exploring radioactively labelled cancerous tissue in a body, comprising an imaging apparatus further comprising a scintillator, a flexible bundle of optical fibers and a position sensitive detector such that the flexible bundle of optical fibers is optically connected to the scintillator at a position inside the body and the flexible bundle of optical fibers is optically connected to the position sensitive detector at a position outside the body, a surgical instrument further comprising a removal or exploratory portion for removing or exploring tissue within the body and a control portion located outside the body for controlling the removal or exploratory portion, such that the scintillator and the removal or exploratory portion are moved about inside the body in tandem while maintaining one of a plurality of relative positions to each other.

This invention also provides an imaging apparatus for creating images of beta radiation emitting objects from within a patient during surgical operations, comprising a plastic scintillator film for receiving beta rays and for converting the beta rays into light signals at a first position located within the patient, a flexible bundle of optical fibers optically connected to the plastic scintillator film for channelling the light signals from the first position to a second position located outside the patient, a position sensitive photomultiplier tube optically connected to the flexible bundle of optical fibers at the second position for receiving the light signals, for converting the light signals into electrons, for multiplying the electrons and for producing analog signals indicative of the relative position of the received light, an electronic circuit for receiving the analog signals, for converting the analog signals into digital signals which correspond to the positions where beta rays impact the plastic scintillator film and for transmitting the digital signals and a computer for receiving, accumulating, manipulating and displaying the digital signals.

Also, this invention provides a position sensitive anode which can comprise a position sensitive crossed-wire anode.

The features, objects and advantages of the invention are described in greater detail below in conjunction with the following drawings.

DETAILED DESCRIPTION OF THE INVENTION

Figure 1:
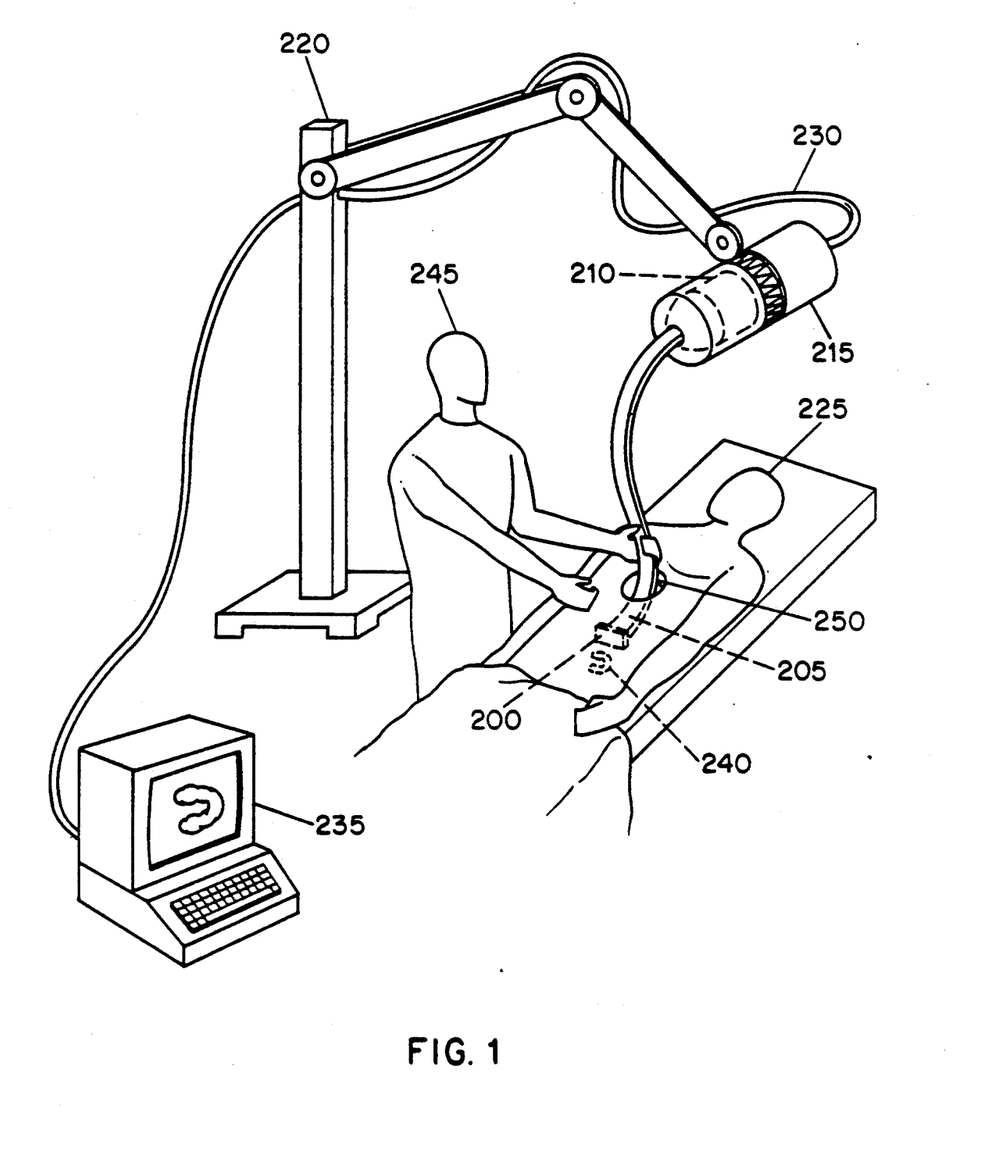
FIG. 1 is a perspective view of an embodiment of the present invention being used during surgery.

FIG. 1 illustrates a surgical use of the present invention. A scintillator 200 is mounted on one end of a flexible bundle of optical fibers 205. The other end of the flexible bundle of optical fibers 205 is connected to a position sensitive photomultiplier tube 210 which is contained in an enclosure 215 which also holds the related electronics for interpreting the signals from the photomultiplier tube 210. This position sensitive photomultiplier tube is held by a support structure 220 which can be placed away from the patient 225. A flexible electrical conduit 230 connects the signals output from the photomultiplier tube 210 to a computer 235 where the image of the radiation producing object, for example a tumor 240, can be displayed. The surgeon 245, therefore, is able to move the flexible bundle of optical fibers 205 inside the patient 225 through a small incision 250. This enables the surgeon 245 to acquire an image of radioactive distribution in the tissue from a much closer location than previously possible thereby enabling detection of tumor deposits on the surface of the operating field. Additionally, the screening of the inside organs of the patient is achieved much faster because the camera's field of view is larger than the field of view of the probe.

Figure 2:
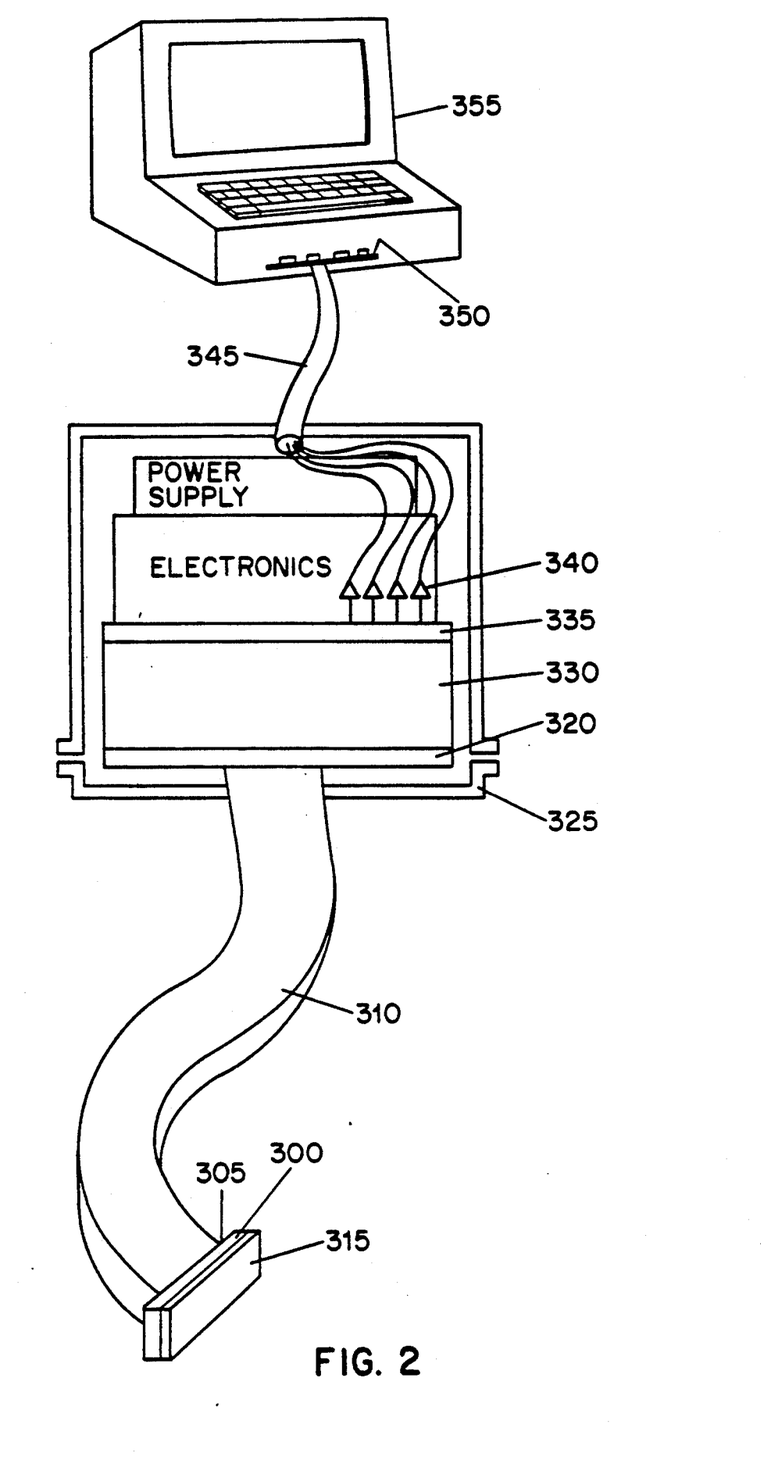
FIG. 2 is a cross section of an embodiment of the present invention.

FIG. 2 shows a cross-section of one embodiment of the present invention. One side of plastic scintillator film 300 is optically connected with optical glue or gel 305 to one end of a bundle of optical fibers 310. A plastic scintillator film 300 is preferred because plastic scintillators are sensitive to beta rays and insensitive to background gamma rays. The dimensions of the plastic scintillator film 300 are 25 millimeters by 20 millimeters which is somewhat larger than the dimensions of the cross section of the flexible bundle of optical fibers 310. The plastic scintillator film 300 is only 1 millimeter thick. The other side of the plastic scintillator film 300 is covered with a thin sheet of aluminized Mylar 315 which is 8 micrometers thick to prevent light from entering the plastic scintillator film 300. The flexible bundle of optical fibers 310 has a minimum of 10 fibers per millimeter and is approximately 70 centimeters long with a cross-section of 20 millimeters by 15 millimeters. The other end of the flexible bundle of optical fibers 310 is connected to approximately the center of a photocathode 320 and is held in place with a cap 325. The photocathode 320 adjoins an electron multiplier 330 which multiplies the received electrons while maintaining their relative positions. The electrons emitted from the electron multiplier 330 are propelled to a position sensitive anode mesh 335. The mesh 335 can be constructed from two parallel layers. Each layer is constructed from a plurality of parallel wires with one end of each wire connected to the adjacent wire by a resistor chain formed along one edge of the layer. These layers are stacked one over the other such that the wires in one layer are perpendicular to the wires in the other layer. The ends of each resistor chain (Xa, Xb, Yc, Yd) are connected to preamplifiers 340. The output of the preamplifiers 340 are connected by an electrical conduit 345 to an electronic circuit 350 which is attached to a computer 355.

Before the surgical procedure begins, the patient is injected with a radioactive marker antibody. For example, to localize metastases which have spread to lymph nodes from colorectal cancer, Iodine-131 labeled A33, F19, and CC49 monoclonal antibodies can be injected or, as a further example, to localize tumor deposits of ovarian cancer on the surface of the peritoneum and in lymph nodes, Iodine-131 labeled MX35 and CC49 monoclonal antibodies can be employed.

When this beta camera is used, the scintillation light generated by interaction of a beta particle with the plastic scintillator film 300 is transmitted to the photocathode 320 through the flexible bundle of optical fibers 310. The electron amplifier 330 multiplies the number of electrons and the position sensitive anode 335 generates electronic signals indicative of the position of the beta ray which was detected. Thus, data that can be used to produce an image of the radiation distribution under the imaging beta probe is obtained.

Although several devices can be used for the electron amplifier 330, such as a microchannel plate, higher energy radiation is difficult to detect. Furthermore, microchannel plates, in particular, require much higher voltages, are sensitive to noise and are relatively expensive.

Accordingly, in one embodiment of the present invention, a position sensitive photomultiplier tube is used to detect, amplify and output the relative position of the incident radiation on the scintillator. When the scintillation light reaches the photocathode of the position sensitive photomultiplier tube, electrons are generated. These electrons are amplified in proximity mesh dynodes, which retain the positional information. The electrons are absorbed in a series of anode wires crossed in the X and Y directions. Position sensitive photomultiplier tubes have a linear response in an active area with a diameter of 5 centimeters. Additionally, the full width at half maximum resolution is 0.3 millimeters. In order to define the position of the incident photons, each anode wire is connected to a point in a resistor chain such that the ratio of the difference of the voltages at both ends of the chain to the sum of these voltages gives the position of the photons reaching that anode wire. An electronic circuit decodes these four signals and determines the coordinates of the scintillation event. The decoding electronic circuit and imaging system are discussed below.

Figure 3:
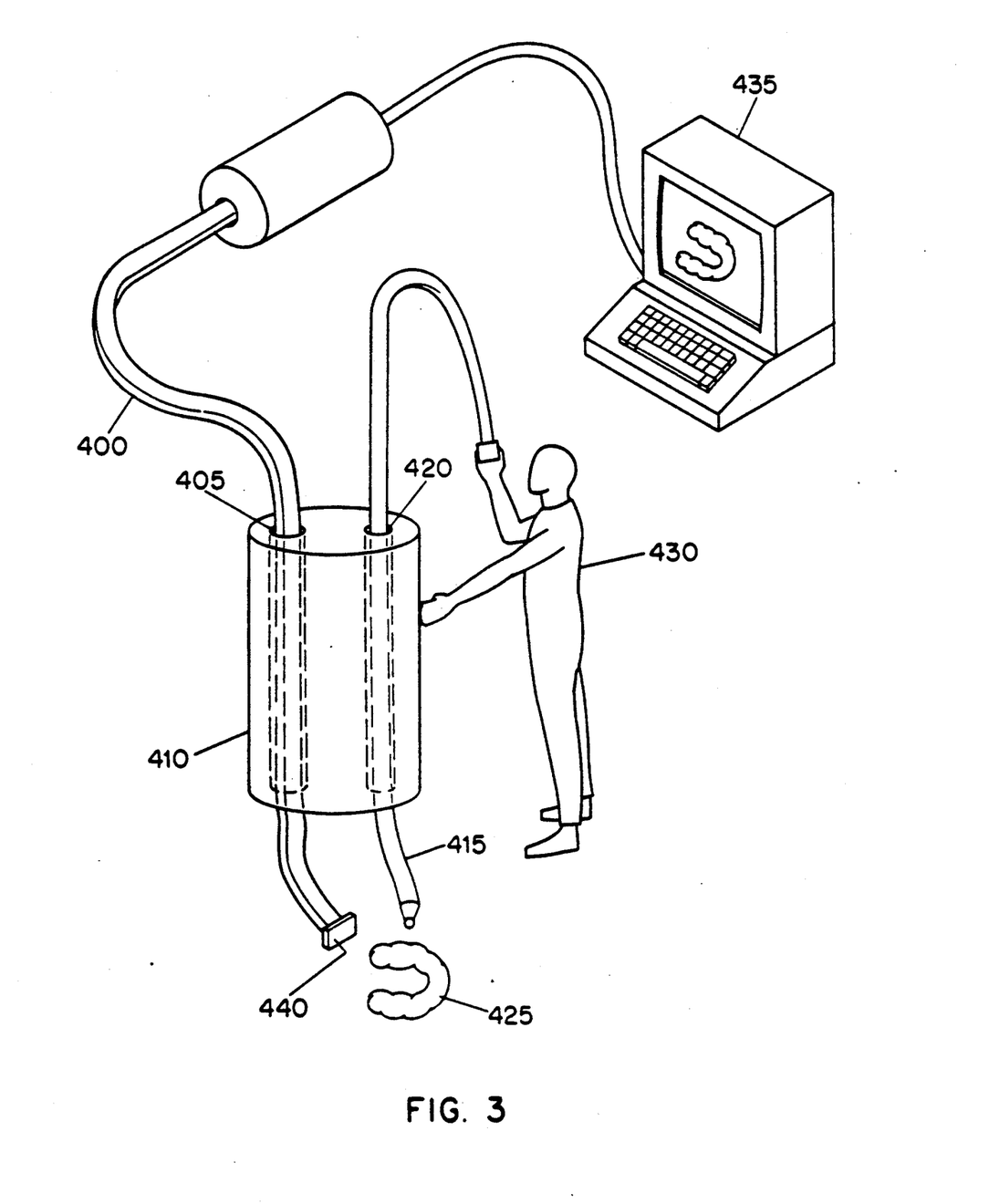
FIG. 3 is a perspective view an embodiment of the present invention.

FIG. 3 illustrates another embodiment of the present invention. Specifically, the flexible bundle of optical fibers 400 is fitted through a lumen 405 in a surgical conduit 410. A tissue removal or exploratory instrument 415, such as, but not limited to, an endoscope, a laparoscope, a laser, a scalpel or a suction device, is fitted through the same lumen 410 or an adjacent lumen 420 for removing or exploring the marked tissue 425 which is made visible to the surgeon 430 on the computer display 425. The flexible bundle of optical fibers 400 can also be attached directly to the tissue removal or exploratory instrument 415. Since the surgical conduit 410 can force the tissue removal or exploratory instrument 415 into fixed spatial relationship with the beta camera's scintillator 440, the surgeon 420 can remove tissue without using a third device for seeing through the surgical conduit 410.

Figure 4:
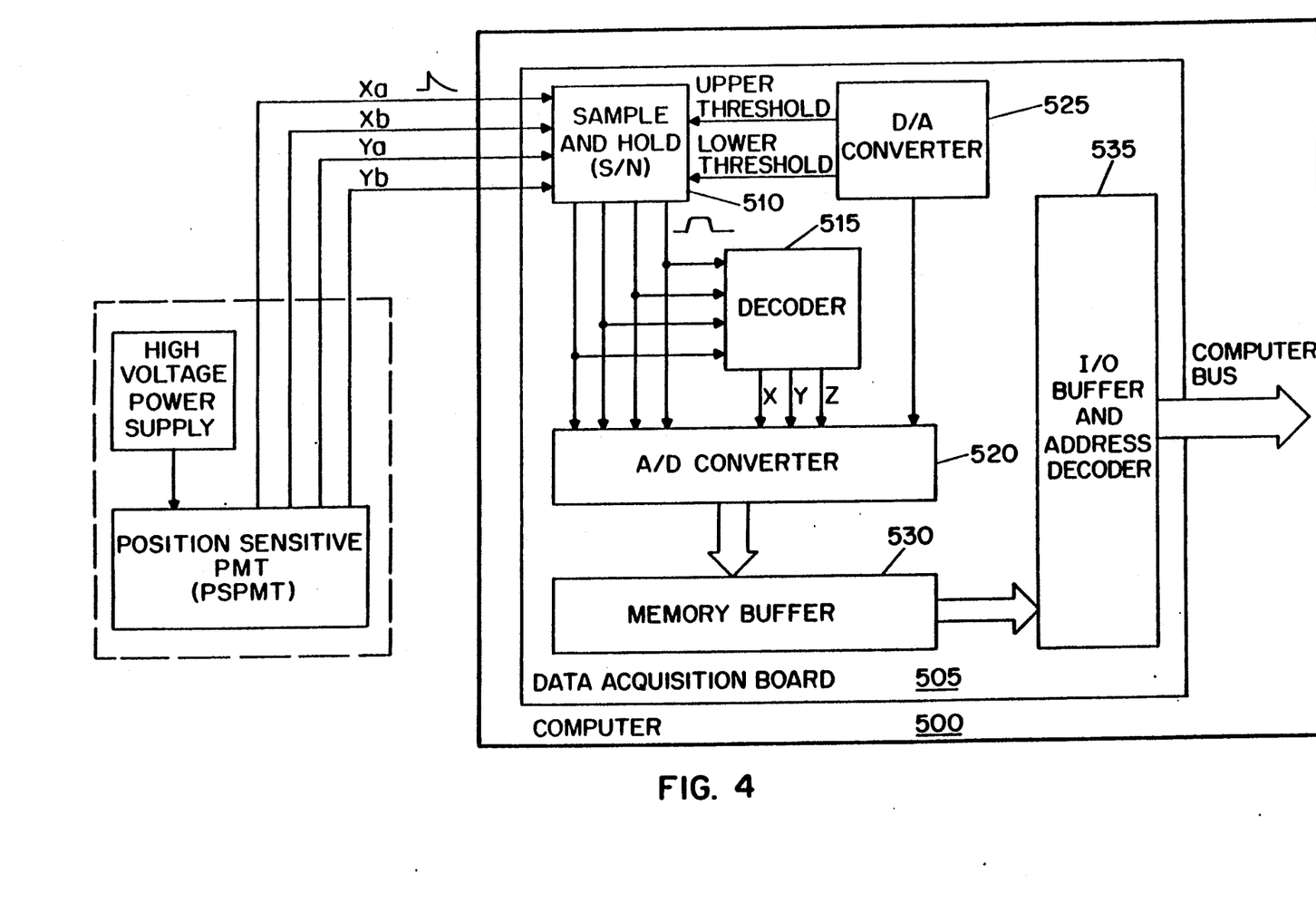
FIG. 4 is a block diagram of the data acquisition equipment used in an embodiment of the present invention.

The electronic circuitry of a current embodiment of the present invention is discussed with reference to FIG. 4. The electronic circuit and imaging system are based on an image acquisition system using an IBM-compatible PC, although any commercially available computer could be used. The image acquisition system consists of a computer 500 and a circuit board 505. The circuit board 505 includes a bi-directional bus buffer 535 along with programmed array logic chips to decode addresses and control bus signals. This circuit board also contains a sample and hold circuit 510, a decoding circuit 515, an analog to digital converter 520, a digital to analog converter 525 and memory chips 530. The sample and hold circuit 510 receives the four signals amplified by the preamplifiers which amplify the signals from the resistor chains mounted on the back of the position sensitive photomultiplier tube. The sample and hold circuit converts these relatively short pulses of amplified position component signals (Xa, Xb, Yc, Yd) into constant signals with longer durations so that the signals can be digitized. The decoding circuit 515 calculates the coordinates (X,Y) of the event from these amplified signals (Xa, Xb, Yc, Yd) according to the following equations: $X=(Xa-Xb)/Z$ and $Y=(Yc-Yd)/Z$, where $Z=Xa+Xb+Yc+Yd$. Z is a measure of the energy deposited by the incident radiation. The CMOS high speed, 8-channel, 8-bit analog-to-digital converter 520 is employed so that the computer 500 can access the four position component signals, decoded X and Y signals, as well as an energy proportional signal. Having these signals digitized and acquired by the PC makes the system very flexible. The upper and the lower energy thresholds are set through software using digital-to-analog converters 525. This allows imaging of those scintillation events that fall in the preset energy window only. Also, intermediate memory chips 530 are employed on the data acquisition board to store information and speed up the system.

The software for controlling the computer and the image acquisition system in one embodiment is written in Microsoft C and Quick BASIC which are relatively fast and easy to use. However, any other computer language may be used. The software allows substantial manipulation of the images. For example, color images, energy spectrums and radioactive concentration profiles can be displayed. Also, one or more images can be focused, shifted, added and subtracted. Additionally, non-uniformities and non-linearities in the images can be corrected.

A miniature high voltage power supply (Hamamatsu C1309-06) is mounted behind the position sensitive photomultiplier tube. This whole assembly is encased in a delrine jacket, except for the light sensitive window which is covered by a cap holding the imaging-grade flexible bundle of optical fibers. This instrument like other intraoperative instruments is placed in a sterile bag during the surgery. In order to ensure the electrical safety of the patient and operators during surgery, all high voltage components are insulated from any metal component within the assembly. Kapton high voltage insulating sheeting is formed around the position sensitive photomultiplier tube, the high voltage power supply and all the related electronics. All the hand held units are sealed with silicone rubber to prevent the entry of moisture that might compromise the operation and safety of the instrument. Additionally, the unit is designed to ensure compliance with the AAMI/ANSI ESI-1985 Safe Current Limits For Electromedical Apparatus. Additionally, because only the non-electrically conducting flexible bundle of optical fibers is placed inside the patient, no electrical contact is made with the patient.

A test of a beta camera was performed using a phantom consisting of multiple holes drilled in a flat lucite block. These holes were 2 millimeters deep, had 1 millimeter diameters and were separated from one another with a center-to-center distance of 3 millimeters. Each hole was filled with Iodine-131 in solution, and covered by a thin plastic tape. The beta camera was placed on top of this phantom and an image was acquired. Other experiments were conducted with phantoms of different patterns. Based on these images the resolution of the beta camera was found to be less than 1 millimeter full width at half maximum. Additionally, the hardware and software which have been developed for this invention increase the field of view of the position sensitive photomultiplier tube to 6 centimeters with a uniformity of better than ±5%. Therefore, larger flexible bundles of optical fibers or multiple flexible bundles of optical fibers can be used with the position sensitive photomultiplier tube.

Other clinical problems addressed by the present invention include, but are not limited to, evaluation of residual cancer in the pelvis during rectal surgery which allows selective use of adjuvant radiation following surgery and the detection of tumor in the abdomen and nodes outside the liver in patients with resectable liver metastases thereby precluding radical life-threatening surgery. This instrument can also be used in many non-cancer related medical procedures.

At this time, at least six different monoclonal antibodies are likely to be used with this invention as markers for tumors in humans. The A33, B72.3 and C110 monoclonal antibodies have already been used and because of their excellent properties MX35, F19 and CC49 should also provide excellent results. Some of the antibodies were developed at Memorial Sloan-Kettering Cancer Center and others are commercial products. However, as new monoclonal antibodies are developed, they also can be used in conjunction with the present invention. In addition, any other radiopharmaceutical that accumulates in tumors can be used. Also, any radioisotope that emits electrons or positrons can be imaged with this camera regardless of its associated gamma radiation.

Other tests show that the beta camera of the present invention is able to detect superficial tumors as small as 10 milligrams. Therefore, this present invention offers the most realistic option in increasing the percentage of tumor removal.

Even though most of the embodiments discussed above referred to the use of the present invention for imaging beta rays, it should be understood that the present invention can also be employed for imaging other types of radiation, such as, for example, gamma rays. Such a flexible intraoperative gamma camera would differ only at the scintillator end of the flexible bundle of optical fibers where a Sodium-Iodine-Thallium scintillator, a collimator and lead or tungsten shielding would be employed.

Although this invention has been described with respect to specific embodiments, many variations based on these specific embodiments can be made by a person of ordinary skill in the art without departing from the spirit of the disclosure or the scope of the appended claims. The embodiments are presented for the purposes of illustration only and should not be read as limiting the invention or its application. Therefore, the claims should be interpreted commensurate with spirit and scope of the invention.

REFERENCES (1) H. B. Barber, J. M. Woolfenden, D. J. Donohue, et al., *Small Radiation Detectors for Bronchoscopic Tumor Localization*, IEEE Trans. Nucl. Sci. Vol. NS-27, pp. 492–502 (1980).

(2) J. M. Woolfenden, W. S. Nevin, H. B. Barber, et al., *Lung cancer detection using a miniature Sodium iodide detector and cobalt-57 bleomycin*. Chest 85:84–88 (1984).

(3) J. M. Woolfenden and H. B. Barber, *Radiation detector probes for tumor localization using tumor-seeking radioactive tracers*. (Review Article) Am. J. Roentgenol., 159:35–39 (1989).

(4) D. T. Martin, G. H. Hinkel, S. Tuttle, et al., *Intraoperative radioimmunodetection of colorectal tumor with a hand-held radiation detector*, Am. J. Surg. 150:672–675 (1985).

(5) P. J. O'Dwyer, C. M. Mojzisik, G. H. Hinkel, et al, *Intraoperative probe directed immunodetection using a monoclonal antibody*, Arch. Surg., 121:1391–1394 (1986).

(6) E. W. Martin, C. M. Mojzisik, G. H. Hinkel, et al., *Radioimmunoguided surgery using monoclonal antibody*, Am. J. Surg., 156:386–392 (1988).

(7) A. Sardi, M. Workman, C. Mojzisik et al., *Intraabdominal recurrence of colorectal cancer detected by radioimmunoguided surgery (RIGS system)*, Arch. Surg., 124:55–59 (1989).

(8) C. A. Nieroda, C. Mojzisik, A. Sardi et al., *The impact of radioimmunoguided surgery (RIGS) on surgical decision-making in colorectal cancer*, Dis. Col. & Rect., 32:927–932 (1989).

(9) H. Reinhardt, D. Stula and O. Gratzl, *Topographic studies with P-32 tumor Marker during Operation of Brain Tumors*, Eur. Surg Res., 17:333–340 (1985).

(10) H. Reinhardt, H. Mayer and E. Amrein, *A Computer-Assisted Device for the intraoperative CT-Correlated Localization of Brain Tumors*, Eur. Sur. Res., 20:51–58 (1988).

(11) H. B. Barber, H. H. Barrett, J. M. Woolfenden, et al., *Comparison of in vivo scintillation probes and gamma cameras for detection of small, deep tumours*, Phys. Med. Biol., 34:727–739 (1989).

(12) T. S. Hickernell, H. B. Barber, H. H. Barrett, et al., *Dual Detector Probe for Surgical Tumor Staging*, J. Nucl. Med. 29:1101–1106 (1988).

(13) N. E. Hartsough, H. B. Barber, J. M. Woolfenden et al., *Probe Containing Gamma Radiation Detectors for in Vivo Tumor Detection and Imaging*, Presented at OE-LASE'89 in Los Angeles, Calif. and to be published in SPIE Vol. 1068.

(14) K. Ljundggren and S. Strand, *Beta Camera for Static and Dynamic Imaging of Charged-Particle Emitting Radionuclides in Biologic Samples*, The Journal of Nuclear Medicine, Vol. 31, No. 12, December 1990.

What is claimed is:

1. An imaging apparatus for creating images of beta ray radiation emitting objects during surgical operations, comprising:

a scintillator means for receiving beta ray radiation and for converting beta ray radiation into light signals;

a flexible bundle of optical fibers having a first end and a second end, the first end optically connected to the scintillator means, the flexible bundle of optical fibers channelling the light signals from the first end to the second end; and a position sensitive light signal detector means optically connected to the second end of the flexible bundle of optical fibers for receiving the light signals and for producing images of the radiation emitting objects;

the flexible bundle of optical fibers allowing the scintillator means to be flexibly moved relative to the position sensitive light signal detector means during surgical operations.

2. An imaging apparatus according to claim 1, wherein the position sensitive light signal detector means comprises:

a photocathode means for receiving the light signals and converting the light signals into electronic signals;

an electronic signal amplifier means connected to the photocathode means for amplifying the electronic signals;

a position sensitive anode means connected to the electronic signal amplifier means for receiving the amplified electronic signals, for determining the location where each light signal was received on the photocathode means and for producing location signals; and a circuit means for receiving the location signals and for producing an image of the beta ray radiation emitting objects.

3. An imaging apparatus according to claim 2, wherein the position sensitive anode means comprises a position sensitive crossed-wire anode.

4. An imaging apparatus according to claim 1, wherein the position sensitive light signal detector means comprises:

a position sensitive photomultiplier tube means for producing location signals indicative of where each light signal was received; and a circuit means for receiving the location signals and for producing an image of the beta ray radiation emitting objects.

5. An imaging apparatus according to claim 1, wherein the scintillator means comprises:

a thin film plastic scintillator sensitive to beta ray radiation and resistant to gamma ray radiation.

6. An imaging apparatus according to claim 5, wherein the circuit means comprises:

an electronic circuit means for receiving the location signals, for converting the location signals into digital signals which correspond to the positions where beta rays impact the thin film plastic scintillator and for transmitting the digital signals; and a computer means for receiving, accumulating, manipulating and displaying the digital signals such that the computer means enables image production, image storage, image comparisons, image combinations and image display.

7. An imaging apparatus according to claim 1, wherein the flexible bundle of optical fibers has a cross-section smaller than the cross-section of the position sensitive light signal detector means, and wherein the flexible bundle of optical fibers is optically connected proximate to the center of a receiving surface of the position sensitive light signal detector means.

8. A surgical apparatus for removing or exploring beta ray emitting radioactively labelled cancerous tissue in a body, comprising:

an imaging apparatus further comprising a scintillator means for receiving radiation and for converting radiation into light signals, a flexible bundle of optical fibers and a position sensitive detector means for receiving the light signals and for producing images of the radiation emitting tissue such that the flexible bundle of optical fibers is optically connected to the scintillator means, the scintillator means being moveable inside the body and the flexible bundle of optical fibers is optically connected to the position sensitive detector means, the position sensitive detector means adapted to be located outside the body;

a surgical instrument further comprising a first instrument means for removing and/or exploring tissue within the body and a second instrument means located outside the body for controlling the first instrument means;

a surgical conduit removably connected to the surgical instrument and the flexible bundle of optical fibers;

such that the scintillator means and the first instrument means are adapted to be moved about inside the body in tandem while maintaining one of a plurality of relative positions to each other.

9. An imaging apparatus for creating images of beta radiation emitting objects from within a patient during surgical operations, comprising:

a plastic scintillator film means for receiving beta rays and for converting the beta rays into light signals at a first position located within the patient;

a flexible bundle of optical fibers optically connected to the plastic scintillator film means, the flexible bundle of optical fibers channelling the light signals from the first position to a second position location outside the patient;

a position sensitive photomultiplier tube means optically connected to the flexible bundle of optical fibers for receiving the light signals, for covering the light signals into electrons, for multiplying the electrons and for producing analog signals indicative of the relative position of the received light;

an electronic circuit means for receiving the analog signals, for converting the analog signals into digital signals which correspond to the positions where beta rays impact the plastic scintillator film means and for transmitting the digital signals; and a computer means for receiving, accumulating, manipulating and displaying the digital signals.

* * * * *